United States Patent
Spaniol et al.

(10) Patent No.: US 12,390,635 B2
(45) Date of Patent: Aug. 19, 2025

(54) RING ELECTRODE FOR A MEDICAL DEVICE

(71) Applicant: Heraeus Deutschland Gmbh & Co. KG, Hanau (DE)

(72) Inventors: Bernd Spaniol, Hanau (DE); Tim Esposto, Hanau (DE); Andre Weigand, Hanau (DE); Markus Jung, Hanau (DE)

(73) Assignee: Heraeus Medevio GmbH & Co. KG, Hanau (DE)

( * ) Notice: Subject to any disclaimer, the term of this patent is extended or adjusted under 35 U.S.C. 154(b) by 1051 days.

(21) Appl. No.: 17/393,950

(22) Filed: Aug. 4, 2021

(65) Prior Publication Data
US 2022/0040474 A1    Feb. 10, 2022

(30) Foreign Application Priority Data
Aug. 4, 2020  (EP) .................................... 20189385

(51) Int. Cl.
*A61N 1/05*     (2006.01)
*A61N 1/36*     (2006.01)
(Continued)

(52) U.S. Cl.
CPC ........... *A61N 1/05* (2013.01); *A61N 1/36125* (2013.01); *B21C 1/003* (2013.01); *B21C 37/065* (2013.01);
(Continued)

(58) Field of Classification Search
CPC ...... A61N 1/05; A61N 1/36125; B21C 1/003; B21C 37/065; B21C 37/154; A61B 2562/125; Y02P 10/25
See application file for complete search history.

(56) References Cited

U.S. PATENT DOCUMENTS 3,267,564  A  *  8/1966  Keyes ....................... B21C 1/22
                                                   D25/120
8,052,744  B2 * 11/2011  Girton ................... A61L 31/146
                                                   623/1.45
(Continued)

FOREIGN PATENT DOCUMENTS

EP       3530314        8/2019
WO    2020/092652      10/2019

*Primary Examiner* — Lawrence Averick
(74) *Attorney, Agent, or Firm* — Dicke, Billig & Czaja, PLLC (57) ABSTRACT

One aspect relates to a process for preparing a ring electrode including the steps of a) providing a monolithic metal precursor, wherein the monolithic metal precursor includes an outer tube forming a first cavity of the precursor, and wherein the outer tube has a wall including in one section an inner tube forming a second cavity of the precursor; b) preparing a composite precursor by inserting a first sacrificial core element into the first cavity of the precursor provided in a) and a second sacrificial core element into the second cavity of the precursor provided in a); c) forming the composite precursor obtained in b) to obtain a formed composite having a smaller outer diameter than the composite precursor obtained in b); d) separating a composite disk from the formed composite obtained in c); e) removing the first and the second sacrificial core element from the composite disk obtained in d).

18 Claims, 2 Drawing Sheets

(51) Int. Cl.
  *B21C 1/00* (2006.01)
  *B21C 37/06* (2006.01)
  *B21C 37/15* (2006.01)

(52) U.S. Cl.
  CPC ...... *B21C 37/154* (2013.01); *A61B 2562/125* (2013.01)

(56) References Cited

U.S. PATENT DOCUMENTS

| | | | |
|---|---|---|---|
| 8,845,713 B2* | 9/2014 | Marton | A61L 31/12 623/1.13 |
| 9,455,373 B2* | 9/2016 | Yokozeki | H10H 20/81 |
| 10,449,030 B2* | 10/2019 | Marton | A61F 2/07 |
| 10,518,001 B2* | 12/2019 | Edick | A61L 31/148 |
| 10,529,815 B2* | 1/2020 | Ando | H10D 64/667 |
| 10,933,233 B2* | 3/2021 | Leitold | A61N 1/362 |
| 10,945,828 B2* | 3/2021 | Marton | A61L 31/022 |
| 2005/0131521 A1* | 6/2005 | Marton | A61F 2/90 623/1.13 |
| 2008/0109072 A1* | 5/2008 | Girton | A61L 31/148 623/1.49 |
| 2012/0046734 A1* | 2/2012 | Girton | A61L 31/148 623/1.42 |
| 2013/0105836 A1* | 5/2013 | Yokozeki | H10H 20/81 257/E33.014 |
| 2014/0277322 A1 | 9/2014 | Victorine et al. | |
| 2015/0021817 A1 | 1/2015 | Romero et al. | |
| 2015/0173885 A1* | 6/2015 | Marton | A61L 27/40 623/1.13 |
| 2016/0166801 A1 | 6/2016 | Birdsall et al. | |
| 2016/0209127 A1* | 7/2016 | Goto | B23P 15/26 |
| 2017/0143220 A1 | 5/2017 | Doerge et al. | |
| 2019/0131418 A1* | 5/2019 | Ando | B82Y 10/00 |
| 2019/0255317 A1* | 8/2019 | Leitold | A61N 1/0551 |
| 2020/0000571 A1* | 1/2020 | Marton | A61F 2/90 |
| 2020/0009372 A1 | 1/2020 | Mercanzini et al. | |

* cited by examiner

RING ELECTRODE FOR A MEDICAL DEVICE

CROSS-REFERENCE TO RELATED APPLICATION

This Utility Patent application claims priority to European Application No. 20 189 385.6 filed on Aug. 4, 2020, which is incorporated herein by reference.

TECHNICAL FIELD

One embodiment relates to a process for preparing a ring electrode or a part thereof, to a composite for preparing a ring electrode or a part thereof, and to a ring electrode or a part thereof. The ring electrode or the part thereof is suitable for use in a medical device, an active implantable medical device, but can also be used for other purposes. The ring electrode or the part thereof can be used for signal acquisition and/or stimulation.

BACKGROUND

Ring electrodes or electrode parts for medical devices, and active implantable medical devices, typically have very small dimensions, and the trend in this technical field is towards further miniaturization.

Conventionally, ring electrodes or electrode parts require very expensive and complex manufacturing equipment and processes with many individual work steps. For example, rings electrodes are often manufactured from a rod material by machining such as turning and the excess material inside the ring is removed, for example by spark erosion. Such conventional preparation processes are costly, and can be limited with regard to the shape of the electrode or the part thereof and in terms of the degree of miniaturization which can be achieved.

In EP 3 530 314 A1, a process for preparing a ring electrode is described including providing an outer element, including an outer tube, providing a first inner element, including a first inner tube having a first core of a sacrificial material, providing a second inner element, including a second core of a sacrificial material, forming a composite tube by arranging the first inner element and the second inner element inside the outer element, the first inner element and the second inner element being arranged off-center with respect to one another, drawing the composite tube in a longitudinal direction of the composite tube, separating a composite tube disk from the composite tube, removing the sacrificial material of the first core, and removing the sacrificial material of the second core. However, using different types of tube components as starting materials, there is always a limitation with respect to the geometry, dimensions and/or shape of the final ring electrode. For example, the geometry of the final ring electrode may be governed by the wall thickness of the tube components. Furthermore, the outer shape of the formed tube components are limited to a circular outer shape.

A process for preparing a ring electrode or a part thereof is desirable, wherein the process allows for preparing an electrode or a part thereof with a higher flexibility and less limitations in terms of the dimensions, geometry and/or shape of the electrode or a part thereof.

For these and other reasons there is a need for the present embodiment.

In view of the foregoing, one embodiment is directed to the provision of an improved, or at least alternative, process for preparing a ring electrode or a part thereof. In particular, one embodiment is directed to the provision of a process for preparing a ring electrode or a part thereof, which provides a higher flexibility and/or less limitations in terms of dimensions, geometry and/or shape of the ring electrode or a part thereof.

SUMMARY

One aspect of one embodiment refers to a process for preparing a ring electrode. The process includes the steps of:
a) providing a monolithic metal precursor,
   wherein the monolithic metal precursor includes an outer tube forming a first cavity of the precursor, and
   wherein the outer tube has a wall including in one section an inner tube forming a second cavity of the precursor;
b) preparing a composite precursor by inserting a first sacrificial core element into the first cavity of the precursor provided in step a) and a second sacrificial core element into the second cavity of the precursor provided in step a);
c) forming the composite precursor obtained in step b) to obtain a formed composite having a smaller outer diameter than the composite precursor obtained in step b);
d) separating a composite disk from the formed composite obtained in step c);
e) removing the first and the second sacrificial core element from the composite disk obtained in step d).

Another object of one embodiment refers to a composite for preparing a ring electrode including
i) a monolithic metal element including an outer tube forming a first cavity, wherein the outer tube has a wall including in one section an inner tube forming a second cavity,
ii) a first sacrificial core element, wherein the first sacrificial core element is located in the first cavity of the monolithic metal element, and
iii) a second sacrificial core element, wherein the second sacrificial core element is located in the second cavity of the monolithic metal element.

Another object of one embodiment relates to a ring electrode for a medical device,
wherein the ring electrode is a monolithic metal,
wherein the ring electrode includes an outer tube forming a first cavity of the electrode,
wherein the outer tube has a wall including in one section an inner tube forming a second cavity of the electrode, and
the wall of the outer tube has at least one section having a thickness of below 150 μm.

The inventors found that by the process according to one embodiment a ring electrode can be prepared which is less limited in terms of dimensions, geometry and/or shape. By using the process according to one the embodiment, it is possible to uniformly form a scaled-up monolithic metal precursor into a longitudinal direction, in order to prepare a ring electrode having essentially the same geometry and/or shape as the precursor, but which has a reduced overall diameter. This is achieved by forming a composite including the monolithic metal precursor and two sacrificial core elements, which are inserted into the cavities of the precursor. After further processing of the composite including the removal of the sacrificial core elements, the ring electrode with the desired dimensions, geometry and/or shape is obtained. The process is very accurate and has very narrow tolerances and/or deviations regarding geometry and/or shape.

It is to be understood that the desired final geometry and shape of the ring electrode can be fully controlled at the level of the scaled-up monolithic metal precursor. The scaled-up monolithic metal precursor can be prepared by a method such as electrically discharge machining (EDM) or metal additive manufacturing (e.g. selective laser melting; selective electron beam melting), which allow for preparing a large variety of different geometries and shapes of a monolithic metal work piece. Hence, the process according to one embodiment gives access to miniaturized ring electrodes with a geometry and/or shape of choice. By conventional techniques, such ring electrodes would only be accessible using very complex and cost intensive processes, if at all possible.

In yet another aspect, one embodiment refers to a process for preparing a ring electrode or a part thereof. The process includes the steps of:

1) providing a sacrificial outer element including a cavity A, wherein the sacrificial outer element, as seen in a radial cross section, has a circular outer shape;
2) providing a monolithic metal precursor including a tube including a cavity B;
3) providing a sacrificial core element;
4) preparing a composite precursor by inserting the monolithic metal precursor into cavity A of the sacrificial outer element, and by inserting the sacrificial core element into cavity B of the monolithic metal precursor;
5) forming the composite precursor obtained in step 4) to obtain a formed composite having a smaller outer diameter than the composite precursor obtained in step 4);
6) separating a composite disk from the formed precursor obtained in step 5);
7) removing the sacrificial outer element and the sacrificial core element from the composite disk obtained in step 6).

According to yet another aspect of one embodiment, a composite for preparing a ring electrode or a part thereof is provided. The composite includes i) a sacrificial outer element including a cavity A, wherein the sacrificial outer element, as seen in a radial cross section, has a circular outer shape,
ii) a monolithic metal element including a tube including a cavity B, wherein the monolithic metal element is located in cavity A of the sacrificial outer element,
iii) a sacrificial core element, wherein the sacrificial core element is located in cavity B of the monolithic metal element.

In a further aspect of one embodiment, a ring electrode or a part thereof for a medical device is provided, wherein the ring electrode or the part thereof includes a tube including a cavity, and
wherein the ring electrode or the part thereof is a monolithic metal, and
wherein the ring electrode or the part thereof, as seen in a radial cross section, has a non-circular outer shape.

The inventors further found that, by the process according to one embodiment, a ring electrode or a part thereof can be prepared which is less limited in terms of its outer shape. More precisely, by using a circular sacrificial outer element which envelopes a monolithic metal precursor having a non-circular or asymmetric outer shape, it is possible to uniformly form the monolithic metal precursor into a longitudinal direction without significantly changing the overall geometry and/or outer shape of the monolithic precursor (besides its diameter of course). This is achieved by preparing a composite including a sacrificial outer element, which envelopes the monolithic metal precursor, and wherein a sacrificial core element is inserted into a cavity of the monolithic precursor. In a subsequent step, the composite is formed. After further processing of the composite including the removal of the sacrificial outer and core element, the ring electrode or the part thereof with the desired dimensions, geometry and/or shape is obtained. As already described above, the desired final geometry and shape of the ring electrode or the part thereof can be fully controlled at the level of a scaled-up monolithic metal precursor.

The general inventive concept of one embodiment is based on the finding that a scaled-up monolithic metal precursor with a desired shape is provided first, and then uniformly formed into a longitudinal direction as part of a composite with sacrificial elements. Thereby, the geometry and/or shape of the monolithic precursor is preserved, and at the same time electrodes and parts thereof are accessible which have very small dimensions.

For the purpose of one embodiment the following terms have the following meanings:

"Monolithic" metal precursor in the meaning of one embodiment means that the metal precursor is prepared from a single metal piece and/or a seamless metal piece, which in one embodiment has a fully merged or homogeneous structure without boundary lines and/or interfaces between different components. A skilled person can determine whether a metal precursor is a monolithic metal precursor e.g. by scanning electron microscopy (SEM).

A "sacrificial" core element or outer element in the meaning of one embodiment is a material which can be selectively removed from a composite including the sacrificial material and the material of the monolithic metal precursor (e.g. the formed composite obtained in step c) or the composite disk obtained in step e) of the inventive process).

Where an indefinite or definite article is used when referring to a singular noun, e.g., "a" "an" or "the", this includes a plural of that noun unless anything else is specifically stated.

Where the term "comprising" is used in the present description and claims, it does not exclude other elements. For the purposes of one embodiment, the terms "essentially consisting of" and "consisting of" are considered to be a preferred embodiments of the term "comprising". If hereinafter a group is defined to comprise at least a certain number of embodiments, this is also to be understood to disclose a group, which preferably essentially consists of only of these embodiments, or preferably consists of only of these embodiments.

Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" in one embodiment.

Whenever the terms "including" or "having" are used, these terms are meant to be equivalent to "comprising" as defined hereinabove.

BRIEF DESCRIPTION OF THE FIGURES

The following figures illustrate aspects of one embodiment for improving the understanding of the invention in connection with some exemplary illustrations, wherein.

DETAILED DESCRIPTION

In the following Detailed Description, reference is made to the accompanying drawings, which form a part hereof, and in which is illustraten by way of illustration specific embodiments in which the embodiment may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiment. The following detailed description, therefore, is not to be taken in a limiting sense, and the scope of the present embodiment is defined by the appended claims.

It is to be understood that the features of the various exemplary embodiments described herein may be combined with each other, unless specifically noted otherwise.

One aspect of one embodiment refers to a process for preparing a ring electrode. The process includes the steps of:
a) providing a monolithic metal precursor,
wherein the monolithic metal precursor includes an outer tube forming a first cavity of the precursor, and
wherein the outer tube has a wall including in one section an inner tube forming a second cavity of the precursor;
b) preparing a composite precursor by inserting a first sacrificial core element into the first cavity of the precursor provided in step a) and a second sacrificial core element into the second cavity of the precursor provided in step a);
c) forming the composite precursor obtained in step b) to obtain a formed composite having a smaller outer diameter than the composite precursor obtained in step b);
d) separating a composite disk from the formed composite obtained in step c);
e) removing the first and the second sacrificial core element from the composite disk obtained in step d).

One embodiment refers to a process for preparing a ring electrode. According to one embodiment, the process is a process for preparing a ring electrode.

The ring electrode may be a circular ring electrode or a hexagonal or octagonal ring electrode. In one embodiment, the ring electrode is a circular ring electrode.

In step a) of the inventive process, a monolithic metal precursor is provided. The monolithic metal precursor includes an outer tube forming a first cavity of the precursor. The outer tube has a wall including in one section an inner tube forming a second cavity of the precursor.

The monolithic metal precursor can be prepared by any known method for preparing and/or machining a monolithic metal work piece. In one embodiment, the monolithic metal precursor is prepared by at least one process selected from the group of electrical discharging machining, additive manufacturing, deep-hole drilling, and milling. It is particularly preferred that the monolithic metal precursor is prepared by electrical discharging machining or additive manufacturing (e.g. selective laser melting; selective electron beam melting), and in one embodiment by electrical discharging machining.

In general, the metal of the monolithic metal precursor may be any metal, which is suitable for a ring electrode. In one embodiment, the metal of the monolithic metal precursor is a biocompatible metal. The term "biocompatible" in the meaning of one embodiment is meant to refer to a material which is considered by a person skilled in the art to be safe when being in contact with a living organism (e.g. a human) over a specific period of time (e.g. when used in an implantable medical device). A skilled person knows or can determine whether a metal may be considered biocompatible or not. For example, the biocompatible metal may be a biocompatible metal according to EN ISO 10993.

According to one embodiment, the metal of the monolithic metal precursor includes, in one embodiment consists of, a metal selected from the group consisting of platinum, gold, iridium, steel, titanium, hafnium, niobium, tantalum, cobalt, nickel, chromium, zirconium, rhenium, tungsten, molybdenum, and alloys of each one of these metals. In one embodiment, the metal is selected from the group consisting of nickel cobalt alloy, steel, platinum and platinum iridium alloy. In one embodiment, the steel is a stainless steel. In one embodiment, the nickel cobalt alloy is MP35N. MP35N is a nickel cobalt alloy including nickel, cobalt, chromium, and molybdenum. In one embodiment, the platinum iridium alloy is Pt/Ir 10 or Pt/Ir20, and in one embodiment Pt/Ir 10.

According to one embodiment, the metal of the monolithic metal precursor is a platinum iridium alloy (e.g. Pt/Ir 10 or Pt/Ir 20).

The monolithic metal precursor includes an outer tube forming a first cavity of the precursor. In one embodiment, the monolithic metal precursor consists of the outer tube forming the first cavity of the precursor.

The outer shape of the outer tube is not particularly limited. However, it is preferred that the outer shape of the outer tube, as seen in a radial cross section, has a circular shape or a hexagonal or octagonal shape. In one embodiment, the outer shape of the outer tube, as seen in a radial cross section, has a circular shape. In case the outer shape of the outer tube has a non-circular and/or asymmetric shape, the process in one embodiment uses an outer sacrificial element as described below for the inventive process including steps 1) to 7).

The outer tube of the monolithic metal precursor provided in step a) can have an outer diameter in the range of 4 to 30 mm, in one embodiment in the range of 5 to 20 mm, in one embodiment in the range of 5 to 12 mm. In one embodiment, the outer tube of the monolithic metal precursor is a circular outer tube having an outer diameter in the range of 4 to 30 mm, in one embodiment in the range of 5 to 20 mm, in one embodiment in the range of 5 to 12 mm. For example, the outer tube of the monolithic metal precursor can have a circular shape and outer diameter of 8 mm.

The first cavity formed by the outer tube, as seen in a radial cross section, is not particularly limited in terms of geometry and/or shape. In other words, the inside of the outer tube of the monolithic metal precursor may have any design, which is suitable for a ring electrode.

The outer tube has a wall including in one section an inner tube forming a second cavity of the precursor. In one embodiment, the inner tube is arranged on the inner side of the outer tube of the monolithic metal precursor provided in step a). This can be understood in that the inner tube does not influence the outer shape of the outer tube. For example, the outer tube may have a circular outer shape, and the wall including in one section the inner tube does not form a protrusion which disturbs the circular outer shape of the outer tube.

According to one embodiment, the outer tube of the monolithic metal precursor provided in step a), as seen in a radial cross section, has a circular outer shape, and the section of the wall of the outer tube which includes the inner tube protrudes into the first cavity of the outer tube. This can be understood in that the wall including in one section the inner tube has a higher thickness than the wall of the outer tube which does not include the inner tube, and in that this thicker wall section protrudes from the inside of the outer tube into the first cavity. This is e.g. also illustrated by FIG. 1. The wall section which includes the inner tube and which protrudes into the first cavity may however have any geometry and/or shape which is required and/or desired for the design of the final ring electrode.

According to one embodiment, the axis of the outer tube extends parallel to the axis of the inner tube in a longitudinal direction.

The outer tube has a wall including in one section an inner tube forming a second cavity of the precursor. The overall wall thickness of the outer tube may be in the range of 0.2 to 10 mm, in one embodiment in the range of 0.4 to 8 mm, in one embodiment 0.4 to 5 mm. In one embodiment, the wall section including the inner tube may have a thickness in the range of 1 to 8 mm, in one embodiment in the range of 1 to 5 mm, and in one embodiment in the range of 1.5 to 3 mm. In one embodiment, the wall of the outer tube has in one section, which does not include the inner tube, a thickness in the range of 0.2 to 2 mm, in one embodiment in the range of 0.4 to 1.5 mm, in one embodiment in the range of 0.4 to 1.0 mm.

The first cavity formed by the outer tube may have one inner diameter in the range of 3 to 29 mm, in one embodiment in the range of 4 to 19 mm, in one embodiment in the range of 4 to 11 mm. The second cavity formed by the inner tube may have one inner diameter in the range of 0.1 to 2 mm, in one embodiment in the range of 0.5 to 1.5 mm, in one embodiment in the range of 0.75 to 1.25 mm.

It is to be understood that the outer tube of the monolithic metal precursor provided in step a) is not limited in that the wall can only include one inner tube as described above. In other words, it is possible, and in certain embodiments preferred, that the outer tube of the monolithic metal precursor provided in step a) includes at least one further inner tube forming at least one further cavity of the monolithic metal precursor in at least one further section of the wall. The design, shape, and dimensions of the at least one further to forming at least one further cavity may be the same or different than the first inner tube forming the second cavity. In one embodiment, the at least one further inner tube has the same design and/or shape as the first inner tube and is arranged in the same way in the outer tube of the precursor.

According to one embodiment, the outer tube of the monolithic metal precursor provided in step a) includes a second inner tube forming a third cavity in another section of the wall of the outer tube. According to another embodiment, the outer tube of the monolithic metal precursor provided in step a) includes a second inner tube forming a third cavity in another section of the wall of the outer tube and a third inner tube forming a fourth cavity and another section of the wall of the outer tube. In case the outer tube includes more than one inner tube (e.g. a second or a third inner tube), it is preferred that the outer tube has a circular outer shape and that the wall sections including the inner tubes are arranged radially on the inside of the outer tube wherein the wall sections protrudes in the first cavity formed by the outer tube.

In step b) of the inventive process, a composite precursor is prepared by inserting a first sacrificial core element into the first cavity of the precursor provided in step a) and a second sacrificial core element into the second cavity of the precursor provided in step a).

In principle, the material of the first and second sacrificial core element may be any material which can be selectively removed from a composite including the sacrificial material and the material of the monolithic metal precursor. Thus, the selection of the material for the sacrificial core elements depends on the metal used for the monolithic metal precursor, and can be selected accordingly.

According to one embodiment, the first sacrificial core element and/or the second sacrificial core element include(s), in one embodiment consists of, a non-noble metal or non-noble metal alloy. A "non-noble" metal or metal alloy in the meaning of the present embodiment is a metal which is not selected from the group of ruthenium, rhodium, palladium, silver, osmium, iridium, platinum, gold, mercury, and alloys of the foregoing metals. According to one embodiment of the present embodiment, the first sacrificial core element and the second sacrificial core element include(s) a non-noble metal or non-noble metal alloy.

In one embodiment, the non-noble metal or non-noble metal alloy is selected from the group of Wood's metal, zinc, tin, nickel, copper, steel, and alloys of each one of these metals. "Wood's metal" is a metal alloy including bismuth, lead, tin and cadmium, and which has a melting point below 100° C. The non-noble metal or non-noble metal alloy may react with acids, in one embodiment strong acids (e.g. sulfuric acid, HCl, nitric acid).

According to one embodiment, the first sacrificial core element and/or the second sacrificial core element include(s), in one embodiment consists of, a metal selected from the group of nickel, copper, steel, and alloys of each one of these metals. According to one embodiment, the first sacrificial core element and the second sacrificial core element include(s), in one embodiment consists of, a metal selected from the group of nickel, copper, steel, and alloys of each one of these metals. In one embodiment, the first sacrificial core element and the second sacrificial core element include(s), in one embodiment consists of, a metal selected from the group of nickel, steel (e.g. stainless steel AISI 316 L), and alloys of these metals.

The inventors surprisingly found that a metal selected from the group of nickel, steel, and alloys of these metals is particularly well-suited as sacrificial core elements, because the materials illustrate a comparatively low diffusion into the monolithic metal precursor during the forming step, and particularly during intermediate annealing steps between or during a drawing process.

The material, in one embodiment the metal, of the first sacrificial core element and the second sacrificial core element may be the same or different. In one embodiment, the materials of the core elements are different. According to one embodiment, the first sacrificial core element includes, in one embodiment consists of, nickel and the second sacrificial core element includes, in one embodiment consists of, steel.

According to one embodiment, the monolithic metal precursor includes, in one embodiment consists of, platinum or a platinum iridium alloy, the first sacrificial core element includes, in one embodiment consists of, nickel and the second sacrificial core element includes, in one embodiment consists of, steel.

The selective removability of the sacrificial core elements from the composite including the monolithic metal precursor, in one embodiment the formed composite obtained in step c) or the composite disk obtained in step e), may be based on a difference in melting point of the materials and/or a difference in chemical reactivity of the materials (e.g. reactivity towards acids or bases). For example, the material of the sacrificial core elements may have a lower melting point than the monolithic metal precursor, so that the sacrificial core elements may be removed by a melting step. Additionally or alternatively, the material of the sacrificial core element may have a higher chemical reactivity, in one embodiment towards acids, than the monolithic metal precursor, so that the sacrificial core elements may be removed by an acid treatment step. A removal of the sacrificial core elements based on a difference in chemical reactivity is preferred over a removal based on a difference in melting points.

According to one embodiment, the first and second sacrificial core elements inserted in step b) include, in one embodiment consists of, a metal, and the metal of the monolithic metal precursor has a higher, i.e. more positive, standard electrode potential than the metal of the first and the second sacrificial core elements. A skilled person knows what the standard electrode potential of a mental is or can look it up. According to the Compendium of Chemical Terminology by the IUPAC, the standard electrode potential is the value of the standard electromotive force of a cell in which molecular hydrogen understand the pressures oxidized to selected protons at the left-hand electrode.

According to one embodiment, the first sacrificial core element inserted in step b) has the dimensions of the first cavity of the monolithic metal precursor provided in step a), and/or the second sacrificial core element inserted in step c) has the dimensions of the second cavity of the monolithic metal precursor provided in step a). "Having the dimensions of" the cavity can be understood in that the first sacrificial core element and/or the second sacrificial core element have near net shape of the first cavity and/or second cavity. According to one embodiment of the present embodiment, the first sacrificial core element inserted in step b) has the dimensions of the first cavity of the monolithic metal precursor provided in step a), and/or the second sacrificial core element inserted in step c) has essentially the dimensions of the second cavity of the monolithic metal precursor provided in step a). In one embodiment, the dimensions of the first sacrificial core element and/or second sacrificial core element, and in one embodiment the outer diameter, are smaller than the dimensions of the first cavity and/or second cavity of the precursor provided in step a) by a factor in the range of 0.01 to 5%, in one embodiment in the range of 0.01 to 3%.

According to one embodiment, the dimensions, and in one embodiment the outer diameter, of the first sacrificial core element and the second sacrificial core element inserted in step b) are smaller than the dimensions of the first cavity and/or second cavity of the precursor provided in step a) by a factor in the range of 0.01 to 5%, in one embodiment in the range of 0.01 to 3%.

The first sacrificial core element and/or the second sacrificial core element inserted in step b) may be prepared by any methods which is suitable for preparing the sacrificial core element such as drawing processes, rolling processes, extrusion, milling, and the like.

The first sacrificial core element and the second sacrificial core element may be inserted in step b) into the cavities of the monolithic metal precursor provided in step a) by any suitable methods known in the art.

In case the monolithic metal precursor provided in step a) includes at least one further inner tube (e.g. a second inner tube or a third inner tube) in at least one further section of the wall of the outer tube, it is to be understood that at least one further sacrificial core element (e.g. a third sacrificial core element or a fourth sacrificial core element) is inserted in step b) into the at least one further inner tube of the monolithic metal precursor provided in step a). The same embodiments defined above in connection with the first and/or second sacrificial core element also apply to the at least one further sacrificial core element.

In step c) of the inventive process, the composite precursor obtained in step b) is formed to obtain a formed composite having a smaller outer diameter than the composite precursor obtained in step b).

The forming in step c) may include at least one process selected from the group of drawing processes, swaging processes, hammering processes and rolling processes. In one embodiment, the forming process is carried out stepwise. The forming parameters in step c) are selected in such a way that in all individual forming steps the stress is introduced into the core of the composite so that all parts of the composite are uniformly deformed into the longitudinal direction during step c).

According to one embodiment, the forming in step c) includes a drawing process. In one embodiment, the drawing process is carried out stepwise, i.e. with multiple individual drawing steps. In one embodiment, the drawing process is carried out with a deformation factor of between 5 and 40%, in one embodiment between 15 and 30%, per individual drawing. It is further preferred that the drawing process is carried out with a die cast having a total included angle 2 $\alpha$ in the range of from 5 to 20°, in one embodiment from 5 to 15°. According to one embodiment, the forming in step c) includes a drawing process, which is carried out with a deformation factor of between 5 and 40%, in one embodiment between 15 and 30%, per individual drawing, and with a die cast having a total included angle 2 $\alpha$ in the range of from 5 to 20°, in one embodiment from 5 to 15°. It is particularly preferred that the deformation factor is in the range of above 20 to 25%, per individual drawing, with a die cast having a total included angle 2 $\alpha$ in the range of from 12 to 15° (e.g. 12°).

According to one embodiment, the forming in step c) includes at least one step of annealing and/or recrystallizing an intermediate formed composite. According to one embodiment, the forming in step c) includes a drawing process, wherein the drawing process includes at least one step of annealing and/or recrystallizing an intermediate formed composite.

Annealing and/or recrystallization steps in metal forming processes are known to the skilled person and can be adjusted based on selected materials of the monolithic metal precursor provided in step a) and the sacrificial core elements. The steps of annealing and/or recrystallizing are carried out in view of the critical degree of transformation of the materials and/or the recrystallization temperature of the materials used in the process. For example, if nickel is used as the first sacrificial core element and/or the second sacrificial core element the critical degree of the formation is about 60% and the recrystallization temperature is about 700° C.

In forming step c), the outer diameter of the monolithic metal precursor provided in step a) being part of the composite obtained in step b) is decreased.

According to one embodiment, the outer diameter of the outer tube of the monolithic metal precursor provided in step a) and the outer diameter of the formed composite obtained in step c) have a ratio which is in the range of 60:1 to 2:1, in one embodiment in the range of 30:1 to 5:1. According to one embodiment, the formed composite obtained in step c) has an outer diameter in the range of 0.2 to 5 mm, in one embodiment of 0.5 to 2 mm.

In step d) of the inventive process, a composite disk is separated from the formed composite obtained in step c).

The composite disk may be separated by any method which is suitable for cutting the material of the monolithic metal precursor and of the sacrificial core elements. For example, a composite disk may be separated from the formed composite obtained in step c) by wire erosion or laser cutting.

In step e) of the inventive process, the first and the second sacrificial core element are removed from the composite disk obtained in step d).

Step e) of the inventive process depends on the material which is used for the first and the second sacrificial core element. According to one embodiment, the first sacrificial element and/or the second sacrificial element is removed in step e) by melting out, etching, corrosion, or combinations thereof. In one embodiment, the first sacrificial element and the second sacrificial element is removed in step e) by melting out, etching, corrosion, or combinations thereof. More in one embodiment, the first sacrificial element and the second sacrificial element is removed in step e) by etching, corrosion, or combinations thereof. Such processes are known to the skilled person, and a skilled person can select the method of removing in step e) in view of the materials used for the first and/or second sacrificial core element.

For example, in case the first and/or second sacrificial core element includes, in one embodiment consists of, a metal having a melting point below 500° C. (e.g. Wood's metal or a zinc or tin alloy), the first and/or second sacrificial core element may be melted out by subjecting the composite disk obtained in step d) to a temperature above the melting point of one of these materials, in one embodiment in the range of 50 to 500° C. The melting out of the sacrificial elements is in one embodiment carried out with vacuum support to overcome the capillary force.

A preferred option is to remove the first and/or second sacrificial core element by treating the composite disk obtained in step d) by an acid (e.g. sulfuric acid, hydrochloric acid, nitric acid) or a base. For example, copper as the first and/or second sacrificial core element may be removed by treatment with nitric acid.

There are also selective etching solutions available for a specific metals being useful as the first and/or second sacrificial core element. Such etching solutions are known to the skilled person and can be selected accordingly.

In case the first sacrificial core element and the second sacrificial core element are different, it is possible to first selectively remove the first sacrificial core element and then selectively remove the second sacrificial core element, or vice versa.

In case, the monolithic metal precursor includes at least one further inner tube (e.g. two or three inner tubes), and the at least one further inner tube includes at least one further sacrificial core element, step e) further includes removing the at least one further sacrificial core element from the composite disk obtained in step d).

In addition to the essential steps a) to e), the inventive process may further include additional process steps of post-processing the ring electrode obtained in step e). For example, after step e), the process may include a further step of washing (e.g. HCl washing) and drying the ring electrode. It is also possible to submit the ring electrode obtained in step e) to a surface finishing step such as polishing, sanding, and/or grinding. In one embodiment, the inventive process includes after step e) the washing, in one embodiment washing with HCl, and drying of the ring electrode followed by a surface finishing step, in one embodiment polishing.

The ring electrode prepared by the inventive process is suitable for use in a medical device, and in one embodiment an active implantable medical device (AIMD). Preferred AIMDs are, for example, cardiac pacemakers, cardiac defibrillators, neurostimulators, cochlea implants, implantable cardioverters, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like. In one embodiment, the active implantable medical device is a cardiac pacemaker or a neuromodulator.

The ring electrode prepared by the inventive process is further suitable for use in a lead for a medical device, in one embodiment an active implantable medical device.

Another object of one embodiment refers to a composite for preparing a ring electrode including i) a monolithic metal element including an outer tube forming a first cavity, wherein the outer tube has a wall including in one section an inner tube forming a second cavity, ii) a first sacrificial core element, wherein the first sacrificial core element is located in the first cavity of the monolithic metal element, and iii) a second sacrificial core element, wherein the second sacrificial core element is located in the second cavity of the monolithic metal element.

Regarding the material, geometry and shape of the monolithic metal element as well as the first and second sacrificial core element, it is referred to the specification of the inventive process above, especially in connection with step a) and step b) of the process. The embodiments, and preferred embodiments, of the monolithic metal precursor provided in step a) of the inventive process are also embodiments, and preferred embodiments, of the monolithic metal element of the composite according to one embodiment. The embodiments, and preferred embodiments, of first and second sacrificial core element inserted in step b) of the inventive process are also embodiments, and preferred embodiments, of the first and second sacrificial core element of the composite according to one embodiment. In this context, it is again pointed out that the inventive process has the advantage that the geometry and shape of the monolithic metal precursor provided in step a) is essentially maintained during and/or after carrying out steps b) to e) of the process. For example, the formed composite obtained in step c) of the inventive process essentially includes a scaled down version of the monolithic metal precursor of step a).

The composite includes a monolithic metal element including an outer tube forming a first cavity, wherein the outer tube has a wall including in one section an inner tube forming a second cavity.

In one embodiment, the wall of the outer tube of the composite has at least one section having a thickness of below 150 µm, and in one embodiment in the range of 10 to 100 µm. It is further preferred that the outer tube of the composite has an outer diameter in the range of 0.2 to 5 mm, and in one embodiment of 0.5 to 2 mm, and/or the first cavity formed by the outer tube has an inner diameter in the range of 0.05 to 4.8 mm, and in one embodiment 0.1 to 1.8 mm, and/or the second cavity formed by the inner tube has an inner diameter in the range of 0.01 to 1.0 mm, and in one embodiment 0.05 to 0.3 mm.

According to one embodiment, the wall of the outer tube of the composite has at least one section having a thickness of below 150 µm, and in one embodiment in the range of 10 to 100 µm, the outer tube of the composite has an outer diameter in the range of 0.2 to 5 mm, and in one embodiment of 0.5 to 2 mm, and the first cavity formed by the outer tube has an inner diameter in the range of 0.05 to 4.8 mm, and in one embodiment 0.1 to 1.8 mm, and the second cavity formed by the inner tube has an inner diameter in the range of 0.01 to 1.0 mm, and in one embodiment 0.05 to 0.3 mm.

Another aspect of one embodiment refers to a ring electrode for a medical device, wherein the ring electrode is a monolithic metal, wherein the ring electrode includes an outer tube forming a first cavity of the electrode, wherein the outer tube has a wall including in one section an inner tube forming a second cavity of the electrode, and wherein the wall of the outer tube has at least one section having a thickness of below 150 µm.

Regarding the material, geometry and shape of the ring electrode, it is referred to the specification of the monolithic metal precursor of the inventive process above, especially in connection with step a) of the process. The embodiments, and preferred embodiments, of the monolithic metal precursor provided in step a) of the inventive process are also embodiments, and preferred embodiments, of the ring electrode according to one embodiment.

The ring electrode according to one embodiment may be a ring electrode having a circular or a hexagonal or octagonal outer shape. In one embodiment, the ring electrode has a circular outer shape The ring electrode being a monolithic metal may be any metal, which is suitable for a ring electrode. In one embodiment the ring electrode is a biocompatible metal. According to one embodiment, the ring electrode includes, in one embodiment consists of, a metal selected from the group consisting of platinum, gold, iridium, steel, titanium, hafnium, niobium, tantalum, cobalt, nickel, chromium, zirconium, rhenium, tungsten, molybdenum, and alloys of each one of these metals. In one embodiment, the metal is selected from the group consisting of nickel cobalt alloy, steel, platinum and platinum iridium alloy. In one embodiment, the steel is a stainless steel. In one embodiment, the nickel cobalt alloy is MP35N. MP35N is a nickel cobalt alloy including nickel, cobalt, chromium, and molybdenum. In one embodiment, the platinum iridium alloy is Pt/Ir 10 or Pt/Ir20, and in one embodiment Pt/Ir 10.

According to one embodiment, the monolithic metal of the ring electrode is a platinum iridium alloy.

The ring electrode is a monolithic metal. "Monolithic metal" means that the metal of the ring electrode is a single metal piece and/or a seamless metal piece, which in one embodiment has a fully merged or homogeneous structure without boundary lines and/or interfaces between different components. However, it is to be understood that this does not exclude that the ring electrode includes a coating. A "coating" for a ring electrode in the meaning of one embodiment is a thin layer, in one embodiment in the range of 0.1 to below 10 µm. Thus, the monolithic metal ring electrode may include a metal coating, a metal oxide coating or a metal nitride coating. The metal of the metal coating metal oxide coating or a metal nitride coating may be the same or different to the metal of the ring electrode. The monolithic metal of the ring electrode may also be coated with a polymer coating. The monolithic metal of the ring electrode may also be surface structured, e.g. laser structured. In principle, the ring electrode of one embodiment may include all surface modifications, which are commonly applied to ring electrodes being used in medical devices, and particularly active implantable medical devices.

The wall of the outer tube has at least one section having a thickness of below 150 µm. according to one embodiment, the wall of the outer tube has at least one section having a thickness in the range of 10 to 100 µm. For example, the wall of the outer tube may have at least one section having a thickness in the range of 10 to 50 µm or in the range of 50 to 90 µm.

In one embodiment, the outer tube of the ring electrode has an outer diameter in the range of 0.2 to 5 mm, and in one embodiment of 0.5 to 2 mm, and/or the first cavity formed by the outer tube has an inner diameter in the range of 0.05 to 4.8 mm, and in one embodiment 0.1 to 1.8 mm, and/or the second cavity formed by the inner tube has an inner diameter in the range of 0.01 to 1.0 mm, and in one embodiment 0.05 to 0.3 mm.

According to one embodiment, the wall of the outer tube has at least one section having a thickness in the range of 10 to 100 µm, the outer tube of the ring electrode has an outer diameter in the range of 0.2 to 5 mm, and in one embodiment of 0.5 to 2 mm, and the first cavity formed by the outer tube has an inner diameter in the range of 0.05 to 4.8 mm, and in one embodiment 0.1 to 1.8 mm, and the second cavity formed by the inner tube has an inner diameter in the range of 0.01 to 1.0 mm, and in one embodiment 0.05 to 0.3 mm.

The outer tube has a wall including in one section an inner tube forming a second cavity of the precursor. In one embodiment, the inner tube is arranged on the inner side of the outer tube of the monolithic metal precursor provided in step a). This can be understood in that the inner tube does not influence the outer shape of the outer tube. For example, the outer tube may have a circular outer shape, and the wall including in one section the inner tube does not form a protrusion which disturbs the circular outer shape of the outer tube.

According to one embodiment, the outer tube of the ring electrode, as seen in a radial cross section, has a circular outer shape, and the section of the wall of the outer tube which includes the inner tube protrudes into the first cavity of the outer tube. This can be understood in that the wall including in one section the inner tube has a higher thickness than the wall of the outer tube which does not include the inner tube, and in that this thicker wall section protrudes from the inside of the outer tube into the first cavity. The wall section which includes the inner tube and which protrudes into the first cavity may have any geometry and/or shape which is required for the design of the final ring electrode. A ring electrode according to the embodiment is e.g. illustrated in FIGS. 3A and 3B.

According to one embodiment, the axis of the outer tube extends parallel to the axis of the inner tube in a longitudinal direction.

It is to be understood that the outer tube of the ring electrode is not limited in that the wall may only include one inner tube as described above. In other words, it is possible, and in certain embodiments preferred, that the outer tube of the ring electrode includes at least one further inner tube forming at least one further cavity of the ring electrode in at least one further section of the wall. The design, shape, and dimensions of the at least one further to forming at least one further cavity may be the same or different than the first inner tube forming the second cavity of the ring electrode. According to one embodiment, the outer tube of the ring electrode includes a second inner tube forming a third cavity in another section of the wall of the outer tube. According to another embodiment, the outer tube of the ring electrode includes a second inner tube forming a third cavity in another section of the wall of the outer tube and a third inner tube forming a fourth cavity and another section of the wall of the outer tube of the ring electrode. In case, the outer tube includes more than one inner tube (e.g. a second or a third inner tube), it is preferred that the outer tube of the ring electrode has a circular outer shape and that the wall sections including the inner tubes are arranged radially on the inside of the outer tube wherein the wall sections protrudes in the first cavity formed by the outer tube.

Another aspect of one embodiment refers to a medical device including a ring electrode. The medical device may be a lead for an active implantable medical device (AIMD). The medical device may also be an active implantable medical device. Preferred AIMDs are, for example, cardiac pacemakers, cardiac defibrillators, neurostimulators, cochlea implants, implantable cardioverters, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like. In one embodiment, the active implantable medical device is a cardiac pacemaker or a neuromodulator.

Another aspect of one embodiment relates to a process for preparing a ring electrode or a part thereof, wherein the process includes the steps of:
1) providing a sacrificial outer element including a cavity A, wherein the sacrificial outer element, as seen in a radial cross section, has a circular outer shape;
2) providing a monolithic metal precursor including a tube including a cavity B;
3) providing a sacrificial core element;
4) preparing a composite precursor by inserting the monolithic metal precursor into cavity A of the sacrificial outer element, and by inserting the sacrificial core element into cavity B of the monolithic metal precursor;
5) forming the composite precursor obtained in step 4) to obtain a formed composite having a smaller outer diameter than the composite precursor obtained in step 4);
6) separating a composite disk from the formed precursor obtained in step 5);
7) removing the sacrificial outer element and the sacrificial core element from the composite disk obtained in step 6).

The inventive process including the steps 1) to 7) can be a process for preparing a ring electrode. In one embodiment, the inventive process including the steps 1) to 7) is a process for preparing a part of a ring electrode. The part of the ring electrode prepared by the inventive process may be used to assemble a ring electrode. According to one embodiment, the inventive process including the steps 1) to 7) is a process for preparing a ring electrode or a part thereof according to the present embodiment.

In steps 1) to 3) of the inventive process, a sacrificial outer element is provided including a cavity A, wherein the sacrificial outer element, as seen in a radial cross section, has a circular outer shape, a monolithic metal precursor including a tube including a cavity B is provided, and a sacrificial core element is provided.

The sacrificial outer element and/or the sacrificial core element may be of any suitable material, which can be selectively removed from a composite including the monolithic metal precursor and the sacrificial elements.

According to one embodiment, the sacrificial outer element and/or the sacrificial core element include(s), in one embodiment consists of, a non-noble metal or non-noble metal alloy. In one embodiment, the non-noble metal or non-noble metal alloy is selected from the group of Wood's metal, zinc, tin, nickel, copper, steel, and alloys of each one of these metals. The non-noble metal or non-noble metal alloy in one embodiment reacts with acids, in one embodiment strong acids (e.g. sulfuric acid, HCl, nitric acid).

According to one embodiment, the sacrificial outer element and/or the sacrificial core element include(s), in one embodiment consists of, a metal selected from the group of nickel, copper, steel, and alloys of each one of these metals. According to one embodiment, the sacrificial outer element and the sacrificial core element include(s), in one embodiment consists of, a metal selected from the group of nickel, copper, steel, and alloys of each one of these metals. In one embodiment, the sacrificial outer element and the sacrificial core element include(s), in one embodiment consists of, a metal selected from the group of nickel, steel (e.g. stainless steel AISI 316 L), and alloys of these metals. The inventors surprisingly found that a metal selected from the group of nickel, steel, and alloys of these metals is particularly well-suited as sacrificial outer element and/or core element, because the materials illustrate a comparatively low diffusion into the monolithic metal precursor during the forming step, and particularly during intermediate annealing steps between or during a drawing process.

The material, in one embodiment the metal, of the sacrificial outer element and the sacrificial core element may be the same or different. In one embodiment, the materials of the core elements are the same. According to one embodiment, the sacrificial outer element and the sacrificial core element include, in one embodiment consist of, steel.

The selective removability of the sacrificial outer element and the sacrificial core element from the composite including the monolithic metal precursor, in one embodiment the formed composite obtained in step 5) or the composite disk obtained in step 7), may be based on a difference in melting point of the materials and/or a difference in chemical reactivity of the materials (e.g. reactivity towards acids or bases). For example, the material of the sacrificial outer element and the sacrificial core element may have a lower melting point than the monolithic metal precursor, so that the sacrificial outer element and the sacrificial core element may be removed by a melting step. Additionally or alternatively, the material of the sacrificial outer element and the sacrificial core element may have a higher chemical reactivity, in one embodiment towards acids, than the monolithic metal precursor, so that the sacrificial outer element and the sacrificial core element may be removed by an acid treatment step. A removal of the sacrificial core elements based on a difference in chemical reactivity is preferred over a removal based on a difference in melting points.

According to one embodiment, the sacrificial outer element and the sacrificial core element include, in one embodiment consists of, a metal, and the metal of the monolithic metal precursor has a higher, i.e. more positive, standard electrode potential than the metal of the sacrificial outer element and the sacrificial core element.

A sacrificial outer element is provided in step 1) including a cavity A, wherein the sacrificial outer element, as seen in a radial cross section, has a circular outer shape.

The dimensions of the cavity A are in one embodiment adjusted to the monolithic metal precursor provided in step 2), and in one embodiment adjusted to the outer shape of the monolithic metal precursor provided in step 2). Hence, according to one embodiment, the cavity A of the sacrificial outer element has the dimensions, or has essentially the dimensions, of the monolithic metal precursor provided in step 2), and in one embodiment of the outer shape of the monolithic metal precursor provided in step 2). According to another embodiment, the dimensions of the cavity A of the sacrificial outer element are larger than the dimensions of the monolithic metal precursor provided in step 2), and in one embodiment of the outer shape of the monolithic metal precursor provided in step 2), by a factor in the range of 0.1 to 5%, and in one embodiment in the range of 0.1 to 3%.

The sacrificial outer element provided in step 1) in one embodiment has an outer diameter in the range of 2 to 30 mm, in one embodiment in the range of 5 to 20 mm. In general, the outer diameter of the sacrificial outer element can be adjusted to the dimensions, in one embodiment the outer shape of the monolithic metal precursor, and with regard to whether a ring electrode is prepared by the inventive process, or a part of a ring electrode. In one embodiment, the sacrificial outer element has an outer diameter in the range of 2 to 12 mm.

The dimensions of the sacrificial core element are in one embodiment adjusted to the dimensions of the cavity B of the tube of the monolithic metal precursor provided in step 2). According to one embodiment, the sacrificial core element has the dimensions, or has essentially the dimensions, of cavity B of the tube of the monolithic metal precursor provided in step 2). According to another embodiment, the dimensions, and in one embodiment the outer diameter, of the sacrificial core element are smaller than the dimensions, in one embodiment the outer diameter, of cavity B of the tube of monolithic metal precursor provided in step 2) by a factor in the range of 0.1 to 5%, and in one embodiment in the range of 0.1 to 3%.

The sacrificial outer element and/or the sacrificial core element may be prepared by any methods which is suitable for preparing the sacrificial elements such as drawing processes, rolling processes, extrusion, milling, and the like.

The monolithic metal precursor provided in step 2) includes a tube including a cavity B, and in one embodiment the monolithic metal precursor consists of the tube including a cavity B. In one embodiment, the monolithic metal precursor consists of the tube including a cavity B.

The monolithic metal precursor provided in step 2) can be prepared by any known method for preparing and/or machining a monolithic metal work piece. In one embodiment, the monolithic metal precursor is prepared by at least one process selected from the group of electrical discharging machining, additive manufacturing, deep-hole drilling, and milling. It is particularly preferred that the monolithic metal precursor is prepared by electrical discharging machining or additive manufacturing (e.g. selective laser melting; selective electron beam melting), and more in one embodiment by electrical discharging machining.

In general, the metal of the monolithic metal precursor may be any metal, which is suitable for a ring electrode. In one embodiment, the metal of the monolithic metal precursor is a biocompatible metal.

According to one embodiment, the metal of the monolithic metal precursor provided in step 2) includes a metal selected from the group consisting of platinum, gold, iridium, steel, titanium, hafnium, niobium, tantalum, cobalt, nickel, chromium, zirconium, rhenium, tungsten, molybdenum, and alloys of each one of these metals. In one embodiment, the metal is selected from the group consisting of nickel cobalt alloy, steel, platinum and platinum iridium alloy. In one embodiment, the steel is a stainless steel. In one embodiment, the nickel cobalt alloy is MP35N. MP35N is a nickel cobalt alloy including nickel, cobalt, chromium, and molybdenum. In one embodiment, the platinum iridium alloy is Pt/Ir 10 or Pt/Ir 20, and in one embodiment Pt/Ir 10. According to one embodiment, the metal of the monolithic metal precursor is a platinum iridium alloy (e.g. Pt/Ir 10 or Pt/Ir 20).

According to one embodiment, the monolithic metal precursor includes, in one embodiment consists of, platinum or a platinum iridium alloy, and the sacrificial outer element and/or the sacrificial core element include, in one embodiment consist of, steel or nickel. According to one embodiment, the monolithic metal precursor includes, in one embodiment consists of, platinum or a platinum iridium alloy, and the sacrificial outer element and the sacrificial core element include, in one embodiment consist of, steel.

It is one advantage of the inventive process of one embodiment that the outer shape of the monolithic metal precursor provided in step 1) is not particularly limited. According to one embodiment, the outer shape of the monolithic metal precursor provided in step 1), as seen in a radial cross section, has a non-circular outer shape. A "non-circular" shape in the meaning of the present embodiment is a shape, as seen in a radial cross section, which has at least two diameters which differ from each other by a factor of at least 2% (e.g. in the range of 2 to 90%), in one embodiment at least 5%, in one embodiment at least 10%. In one embodiment, the outer shape of the monolithic metal precursor provided in step 1), as seen in a radial cross section, is an oval, polygonal, cubic or rectangular outer shape.

The monolithic metal precursor provided in step 2), as seen in a radial cross section, may have an outer diameter in the range of 1 to 25 mm, in one embodiment in the range of 1 to 20 mm. The outer diameter will depend on whether it is desired that a ring electrode is to be prepared or a part thereof. In one embodiment, the monolithic metal precursor provided in step 2), as seen in a radial cross section, has an outer diameter in the range of 1 to 10 mm.

It is further possible, and in some embodiments preferred, that the cavity B of the monolithic metal precursor, as seen in a radial cross section, has a different shape than the outer shape of the monolithic metal precursor. In one embodiment, the cavity B of the monolithic metal precursor, as seen in a radial cross section, has a circular shape. For example, the outer shape of the monolithic metal precursor, as seen in a radial cross section, may be oval, and the cavity B of the monolithic metal precursor, as seen in a radial cross section, may have a circular shape.

According to one embodiment, cavity B has an inner diameter in the range of 3 to 29 mm, in one embodiment in the range of 4 to 19 mm, in one embodiment in the range of 4 to 11 mm. However, it is also possible that the cavity B has a smaller inner diameter, especially if a part of a ring electrode is to prepared. Thus, in another embodiment, cavity B has an inner diameter in the range of 0.1 to 4 mm, in one embodiment in the range of 0.5 to 1.5 mm, in one embodiment in the range of 0.75 to 1.25 mm.

According to one embodiment, the outer shape of the monolithic metal precursor, as seen in a radial cross section, has a non-circular outer shape, and in one embodiment an oval, polygonal, cubic or rectangular outer shape, and the cavity B of the monolithic metal precursor, as seen in a radial cross section, has a different shape than the outer shape of the monolithic metal precursor, and in one embodiment a circular shape.

The monolithic metal precursor provided in step 2) is not limited in that the monolithic metal precursor can only have one cavity. It is to be understood that the monolithic metal precursor can also have more than one cavity. In particular, the monolithic metal precursor provided in step 2) can have at least one further cavity in at least one section of the wall, wherein the at least one further cavity forms an inner tube in the at least one section of the wall. Thus, the monolithic metal precursor can be a monolithic metal precursor as provided in step a) of the inventive process. Therefore, according to one embodiment, the monolithic metal precursor provided in step 2) is the same monolithic metal precursor as provided in step a) of the inventive process, or in one embodiment of the monolithic metal precursor is provided in step a). According to one embodiment, the monolithic metal precursor provided in step 2) is the same monolithic metal precursor as provided in step a) of the inventive process, wherein the monolithic metal precursor has a non-circular outer shape. The skilled person reading the specification of the present invention understands which adjustments have to be made to the inventive process, in case the monolithic metal precursor provided in step 2) has at least one further cavity and at least one section of its wall (e.g. at least one further sacrificial core element as defined herein has to be provided, removal of the at least one further sacrificial core element in step 7) etc.).

In step 4) of the inventive process, a composite precursor is prepared by inserting the monolithic metal precursor into cavity A of the sacrificial outer element, and by inserting the sacrificial core element into cavity B of the monolithic metal precursor. A skilled person will select the appropriate method for inserting and/or assembling the different components to prepare the composite precursor of step 4).

In step 5) of the inventive process, the composite precursor obtained in step 4) is formed to obtain a formed composite having a smaller outer diameter than the composite precursor obtained in step 4).

The forming in step 5) may include at least one process selected from the group of drawing processes, swaging processes, hammering processes and rolling processes. In one embodiment, the forming process is carried out stepwise. The forming parameters in step 5) are selected in such a way that in all individual forming steps the stress is introduced into the core of the composite so that all parts of the composite are uniformly deformed into the longitudinal direction during step 5). According to one embodiment, the forming in step 5) includes a drawing process. In one embodiment, the drawing process is carried out stepwise, i.e. with multiple individual drawing steps.

In one embodiment, the drawing process is carried out with a deformation factor of between 5 and 40%, in one embodiment between 15 and 30%, per individual drawing. It is further preferred that the drawing process is carried out with a die cast having a total included angle $2\alpha$ in the range of from 5 to 20°, in one embodiment from 5 to 15°.

According to one embodiment, the forming in step 5) includes a drawing process, which is carried out with a deformation factor of between 5 and 40%, in one embodiment between 15 and 30%, per individual drawing, and with a die cast having a total included angle $2\alpha$ in the range of from 5 to 20°, in one embodiment from 5 to 15°. It is particularly preferred that the deformation factor is in the range of above 20 to 25%, per individual drawing, with a die cast having a total included angle $2\alpha$ in the range of from 12 to 15° (e.g. 12°).

According to one embodiment, the forming in step 5) includes at least one step of annealing and/or recrystallizing an intermediate formed composite. According to one embodiment, the forming in step 5) includes a drawing process, wherein the drawing process includes at least one step of annealing and/or recrystallizing an intermediate formed composite. Annealing and/or recrystallization steps in metal forming processes are known to the skilled person and can be adjusted based on selected materials of the components provided in step 1) to 3). The steps of annealing and/or recrystallizing are carried out in view of the critical degree of transformation of the materials and/or the recrystallization temperature of the materials used in the process. For example, if nickel is used as the first sacrificial core element and/or the second sacrificial core element the critical degree of the formation is about 60% and the recrystallization temperature is about 700° C.

In forming step 5), the outer diameter of the sacrificial outer element provided in step 1) being part of the composite obtained in step 4) is decreased. According to one embodiment, the outer diameter of the sacrificial outer element provided in step 1) and the outer diameter of the formed composite obtained in step 5) have a ratio which is in the range of 60:1 to 2:1, in one embodiment in the range of 30:1 to 5:1. According to one embodiment, the formed composite obtained in step 5) has an outer diameter in the range of 0.2 to 5 mm, in one embodiment of 0.5 to 2 mm.

In step 6) of the inventive process, a composite disk is separated from the formed precursor in step 5). The composite disk may be separated by any method which is suitable for cutting the material of the monolithic metal precursor and of the sacrificial elements. For example, a composite disk may be separated from the formed composite obtained in step 5) by wire erosion or laser cutting.

In step 7) of the inventive process, the sacrificial outer element and the sacrificial core element are removed from the composite disk obtained in step 6). Step 7) of the inventive process depends on the material which is used for the sacrificial outer element and the sacrificial core element. According to one embodiment, the sacrificial outer element and/or the sacrificial core element is removed in step e) by melting out, etching, corrosion, or combinations thereof. In one embodiment, the sacrificial outer element and the sacrificial core element are removed in step 7) by melting out, etching, corrosion, or combinations thereof.

For example, in case the sacrificial outer element and the sacrificial core element includes, in one embodiment consists of, a metal having a melting point below 500° C. (e.g. Wood's metal or a zinc or tin alloy), the sacrificial outer element and the sacrificial core element may be melted out by subjecting the composite disk obtained in step 6) to a temperature above the melting point of one of these materials, in one embodiment in the range of 50 to 500° C. The melting out of the sacrificial elements is in one embodiment carried out with vacuum support to overcome the capillary force.

A preferred option is to remove the sacrificial outer element and the sacrificial core element by treating the composite disk obtained in step 6) by an acid (e.g. sulfuric acid, hydrochloric acid, nitric acid) or a base. There are also selective etching solutions available for a specific metals being useful as the sacrificial outer element and the sacrificial core element.

According to another aspect of one embodiment, a composite for preparing a ring electrode or a part thereof is provided, wherein the composite includes
i) a sacrificial outer element including a cavity A', wherein the sacrificial outer element, as seen in a radial cross section, has a circular outer shape,
ii) a monolithic metal element including a tube including a cavity B', wherein the monolithic metal element is located in cavity A' of the sacrificial outer element,
iii) a sacrificial core element, wherein the sacrificial core element is located in cavity B' of the monolithic metal element.

Regarding the material, geometry and shape of the monolithic metal element as well as the sacrificial outer element and the sacrificial core element, it is referred to the specification of the inventive process above, especially in connection with steps 1) to 3) of the process. The embodiments, and preferred embodiments, of the monolithic metal precursor provided in step 2) of the inventive process are also embodiments, and preferred embodiments, of the monolithic metal element of the composite according to one embodiment. The embodiments, and preferred embodiments, of the sacrificial outer element and the sacrificial core element provided in step 1) and 3) of the inventive process are also embodiments, and preferred embodiments, of the first and second sacrificial core element of the composite according to the present invention. The inventive process according to one embodiment has the advantage that the geometry and shape of the monolithic metal precursor provided in step 2) is essentially maintained during and/or after carrying out steps 4) to 7) of the process. The formed composite obtained in step 5) of the inventive process essentially includes a scaled down version of the monolithic metal precursor of step 2).

According to one embodiment, the monolithic element, as seen in a radial cross section, has a non-circular outer shape. In one embodiment, the monolithic element has an oval, polygonal, cubic or rectangular outer shape. According to another embodiment, the cavity B', as seen in a radial cross section, has a shape which is different to the outer shape of the monolithic element. In one embodiment, the cavity B', as seen in a radial cross section, has a circular shape. According to one embodiment, the monolithic element, as seen in a radial cross section, has a non-circular outer shape, and in one embodiment an oval, polygonal, cubic or rectangular outer shape, and the cavity B' has a shape which is different to the outer shape of the monolithic element, and in one embodiment has a circular shape.

In one embodiment, the monolithic element of the inventive composite has a wall, which at least in one section has a thickness of below 150 µm, and in one embodiment in the range of 10 to 100 µm. It is further preferred that the monolithic element has at least one outer diameter in the range of 0.1 to 4 mm, and in one embodiment of 0.2 to 2 mm, and/or that the cavity B' has an inner diameter in the range of 0.01 to 3.8 mm, and in one embodiment 0.05 to 1.8 mm.

According to one embodiment, the monolithic element, as seen in a radial cross section, has a non-circular outer shape, and in one embodiment an oval, polygonal, cubic or rectangular outer shape, the cavity B' has a shape which is different to the outer shape of the monolithic element, and in one embodiment has a circular shape, the monolithic element has a wall, which at least in one section has a thickness of below 150 µm, and in one embodiment in the range of 10 to 100 µm, the monolithic element has at least one outer diameter in the range of 0.1 to 4 mm, and in one embodiment of 0.2 to 2 mm, and the cavity B' has an inner diameter in the range of 0.01 to 3.8 mm, and in one embodiment 0.05 to 1.8 mm.

Yet another aspect of one embodiment relates to a ring electrode or a part thereof for a medical device, wherein the ring electrode or the part thereof includes a tube including a cavity, wherein the ring electrode or the part thereof is a monolithic metal, and wherein the ring electrode or the part thereof, as seen in a radial cross section, has a non-circular outer shape.

In one embodiment, the ring electrode or the part thereof consists of a tube including a cavity, wherein the ring electrode or the part thereof is a monolithic metal, and wherein the ring electrode or the part thereof, as seen in a radial cross section, has a non-circular outer shape.

Regarding the material, geometry and shape of the ring electrode or the part thereof, it is referred to the specification of the monolithic metal precursor of the inventive process above, especially in connection with step 2) of the process. The embodiments of the monolithic metal precursor provided in step 2) of the inventive process are also embodiments, and of the ring electrode according to the present embodiments.

The ring electrode or the part thereof being a monolithic metal may be any metal, which is suitable for a ring electrode or a part thereof. In one embodiment the ring electrode or the part thereof is a biocompatible metal. According to one embodiment, the ring electrode or the part thereof includes, in one embodiment consists of, a metal selected from the group consisting of platinum, gold, iridium, steel, titanium, hafnium, niobium, tantalum, cobalt, nickel, chromium, zirconium, rhenium, tungsten, molybdenum, and alloys of each one of these metals. In one embodiment, the metal is selected from the group consisting of nickel cobalt alloy, steel, platinum and platinum iridium alloy. In one embodiment, the steel is a stainless steel. In one embodiment, the nickel cobalt alloy is MP35N. MP35N is a nickel cobalt alloy including nickel, cobalt, chromium, and molybdenum. In one embodiment, the platinum iridium alloy is Pt/Ir 10 or Pt/Ir 20, and in one embodiment Pt/Ir 10. According to one particularly embodiment, the monolithic metal of the ring electrode or the part thereof is a platinum iridium alloy.

The ring electrode or the part thereof is a monolithic metal. "Monolithic metal" means that the metal of the ring electrode or part thereof is a single metal piece and/or a seamless metal piece, which in one embodiment has a fully merged or homogeneous structure without boundary lines and/or interfaces between different components. However, it is to be understood that this does not exclude that the ring electrode includes a coating. A "coating" for a ring electrode or part thereof in the meaning of one embodiment is a thin layer, in one embodiment in the range of 0.1 to below 10 µm. Thus, the monolithic metal ring electrode or part thereof may include a metal coating, a metal oxide coating or a metal nitride coating. The metal of the metal coating metal oxide coating or a metal nitride coating may be the same or different to the metal of the ring electrode. The monolithic metal of the ring electrode or part thereof may also be coated with a polymer coating. The monolithic metal of the ring electrode or part thereof may also be surface structured, e.g. laser structured.

The ring electrode or the part thereof, as seen in a radial cross section, has a non-circular outer shape. According to one embodiment, the ring electrode or the part thereof, as seen in a radial cross section, has an oval, polygonal, cubic or rectangular outer shape. In one embodiment, the ring electrode or the part thereof, as seen in a radial cross section, has an oval outer shape.

The shape of the cavity of the tube of the ring electrode or the part thereof, as seen in a radial cross section, is independent of the outer shape of the ring electrode or the part thereof. In one embodiment, the shape of the cavity, as seen in a radial cross section, is different to the outer shape of the ring electrode or the part thereof. In one embodiment, the cavity has a circular shape.

According to one embodiment, the ring electrode or the part thereof, as seen in a radial cross section, has an oval, polygonal, cubic or rectangular outer shape, in one embodiment an oval shape, and the shape of the cavity, as seen in a radial cross section, is different to the outer shape of the ring electrode or the part thereof, and in one embodiment is circular.

The ring electrode or the part thereof can have specific dimensions. In one embodiment, the tube of the ring electrode or of the part thereof has a wall, which at least in one section has a thickness of below 150 μm, and in one embodiment in the range of 10 to 100 μm. It is further preferred that the tube of the ring electrode or of the part thereof has at least one outer diameter in the range of 0.1 to 4 mm, and in one embodiment of 0.2 to 2 mm, and/or the cavity of the tube has an inner diameter in the range of 0.01 to 3.8 mm, and in one embodiment 0.05 to 1.8 mm.

According to one embodiment, the tube of the ring electrode or of the part thereof has a wall, which at least in one section has a thickness of below 150 μm, and in one embodiment in the range of 10 to 100 μm, and at least one outer diameter in the range of 0.1 to 4 mm, and in one embodiment of 0.2 to 2 mm, and the cavity of the tube has an inner diameter in the range of 0.01 to 3.8 mm, and in one embodiment 0.05 to 1.8 mm.

Another aspect of one embodiment refers to a medical device including a ring electrode or a part thereof. The medical device may be a lead for an active implantable medical device (AIMD). The medical device may also be an active implantable medical device. Preferred AIMDs are, for example, cardiac pacemakers, cardiac defibrillators, neurostimulators, cochlea implants, implantable cardioverters, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like. More in one embodiment, the active implantable medical device is a cardiac pacemaker or a neuromodulator.

The present invention further refers to the aspects and embodiments as defined in the following paragraphs:

[1] A process for preparing a ring electrode, preferably a ring electrode according to any one of paragraphs [17] to [19], comprising the steps of:
  a) providing a monolithic metal precursor,
    wherein the monolithic metal precursor comprises an outer tube forming a first cavity of the precursor, and
    wherein the outer tube has a wall comprising in one section an inner tube forming a second cavity of the precursor;
  b) preparing a composite precursor by inserting a first sacrificial core element into the first cavity of the precursor provided in step a) and a second sacrificial core element into the second cavity of the precursor provided in step a);
  c) forming the composite precursor obtained in step b) to obtain a formed composite having a smaller outer diameter than the composite precursor obtained in step b);
  d) separating a composite disk from the formed composite obtained in step c);
  e) removing the first and the second sacrificial core element from the composite disk obtained in step d).

[2] The method according to paragraph [1], wherein the monolithic metal precursor is prepared by at least one process selected from the group of electrical discharging machining, additive manufacturing, deep-hole drilling, and milling.

[3] The method according to paragraph [1] or [2], wherein the monolithic metal precursor comprises a metal selected from the group consisting of platinum, gold, iridium, steel, titanium, hafnium, niobium, tantalum, cobalt, nickel, chromium, zirconium, rhenium, tungsten, molybdenum, and alloys of each one of these metals, more preferably selected from the group consisting of nickel cobalt alloy, steel, platinum and platinum iridium alloy, and most preferably is a platinum iridium alloy.

[4] The method according to any one of the paragraphs [1] to [3], wherein the inner tube is arranged on the inner side of the outer tube of the monolithic metal precursor provided in step a), and/or
  wherein the outer tube of the monolithic metal precursor provided in step a), as seen in a radial cross section, has a circular outer shape, and the section of the wall of the outer tube which comprises the inner tube protrudes into the first cavity of the outer tube.

[5] The method according to any one of the paragraphs [1] to [4], wherein the outer tube of the monolithic metal precursor provided in step a) has an outer diameter in the range of 4 to 30 mm, preferably in the range of 5 to 20 mm

[6] The method according to any one of the paragraphs [1] to [5], wherein the first sacrificial core element and/or the second sacrificial core element comprise(s) a non-noble metal or non-noble metal alloy, preferably selected from the group of nickel, copper, steel, and alloys of each one of these metals.

[7] The method according to any one of the paragraphs [1] to [6], wherein the first and second sacrificial core elements inserted in step b) comprise a metal, and
  wherein the metal of the monolithic metal precursor has a higher standard electrode potential than the metal of the first and the second sacrificial core elements.

[8] The method according to any one of the paragraphs [1] to [7], wherein the first sacrificial core element inserted in step b) has the dimensions of the first cavity of the monolithic metal precursor provided in step a), and/or
  wherein the second sacrificial core element inserted in step b) has the dimensions of the second cavity of the monolithic metal precursor provided in step a).

[9] The method according to any one of the paragraphs [1] to [8], wherein step c) comprises a drawing process, which is preferably carried out with a deformation factor of between 5 and 40%, preferably between 15 and 30%, per individual drawing, and/or a die cast having a total included angle 2 α in the range of from 5 to 20°, preferably from 5 to 15°.

[10] The method according to any one of the paragraphs [1] to [9], wherein step c) comprises at least one step of annealing and/or recrystallizing an intermediate formed composite.

[11] The process according to any one of paragraphs [1] to [10],
wherein the outer tube of the monolithic metal precursor provided in step a) comprises at least one further inner tube forming at least one further cavity of the monolithic metal precursor in at least one further section of the wall,
wherein step b) further comprises inserting at least one further sacrificial core element in the at last one further cavity of the precursor, and
wherein step e) further comprises removing the at least one further sacrificial core element from the composite disk obtained in step d).

[12] The process according to any one of paragraphs [1] to [11], wherein the outer diameter of the outer tube of the monolithic metal precursor provided in step a) and the outer diameter of the formed composite obtained in step c) have a ratio which is in the range of 60:1 to 2:1, preferably in the range of 30:1 to 5:1.

[13] The process according to any one of paragraphs [1] to [12], wherein the formed composite obtained in step c) has an outer diameter in the range of 0.2 to 5 mm, preferably of 0.5 to 2 mm

[14] The process according to any one of paragraphs [1] to [13], wherein the first sacrificial element and/or the second sacrificial element is removed in step e) by melting out, etching, corrosion, or combinations thereof.

[15] The process according to any one of paragraphs [1] to [14], wherein the process is a process for preparing a ring electrode for a medical device, preferably an active implantable medical device.

[16] A composite for preparing a ring electrode comprising
i) a monolithic metal element comprising an outer tube forming a first cavity,
wherein the outer tube has a wall comprising in one section an inner tube forming a second cavity,
ii) a first sacrificial core element, wherein the first sacrificial core element is located in the first cavity of the monolithic metal element, and
iii) a second sacrificial core element, wherein the second sacrificial core element is located in the second cavity of the monolithic metal element.

[17] A ring electrode for a medical device,
wherein the ring electrode is a monolithic metal,
wherein the ring electrode comprises an outer tube forming a first cavity of the electrode,
wherein the outer tube has a wall comprising in one section an inner tube forming a second cavity of the electrode, and
the wall of the outer tube has at least one section having a thickness of below 150 μm.

[18] The ring electrode according to paragraph [17], wherein the wall of the outer tube has at least one section having a thickness in the range of 10 to 100 μm.

[19] The ring electrode according to paragraph [17] or [18], wherein the outer tube of the ring electrode has an outer diameter in the range of 0.2 to 5 mm, and preferably of 0.5 to 2 mm, and/or
wherein the first cavity formed by the outer tube has an inner diameter in the range of 0.05 to 4.8 mm, and preferably 0.1 to 1.8 mm, and/or
wherein the second cavity formed by the inner tube has an inner diameter in the range of 0.01 to 1.0 mm, and preferably 0.05 to 0.3 mm

[20] A medical device comprising a ring electrode according to any one of paragraphs [17] to [19].

[21] A process for preparing a ring electrode or a part thereof, preferably a ring electrode or part thereof according to paragraph [30] to [33], wherein the process comprises the steps of:
1) providing a sacrificial outer element comprising a cavity A, wherein the sacrificial outer element, as seen in a radial cross section, has a circular outer shape;
2) providing a monolithic metal precursor comprising a tube comprising a cavity B;
3) providing a sacrificial core element;
4) preparing a composite precursor by inserting the monolithic metal precursor into cavity A of the sacrificial outer element, and by inserting the sacrificial core element into cavity B of the monolithic metal precursor;
5) forming the composite precursor obtained in step 4) to obtain a formed composite having a smaller outer diameter than the composite precursor obtained in step 4);
6) separating a composite disk from the formed precursor obtained in step 5);
7) removing the sacrificial outer element and the sacrificial core element from the composite disk obtained in step 6).

[22] The process according to paragraph [21], wherein the outer shape of the monolithic metal precursor, as seen in a radial cross section, has a non-circular outer shape, and preferably an oval, polygonal, cubic or rectangular outer shape, and/or
wherein the cavity B of the monolithic metal precursor, as seen in a radial cross section, has a different shape than the outer shape of the monolithic metal precursor, and preferably a circular shape.

[23] The process according to paragraph [21] or [22], wherein the monolithic metal precursor is prepared by at least one process selected from the group of electrical discharging machining, additive manufacturing, deep-hole drilling and milling.

[24] The process according to any one of paragraphs [21] to [23], wherein the monolithic metal precursor comprises a metal selected from the group consisting of platinum, gold, iridium, steel, titanium, hafnium, niobium, tantalum, cobalt, nickel, chromium, zirconium, rhenium, tungsten, molybdenum, and alloys of each one of these metals, more preferably selected from the group consisting of nickel cobalt alloy, steel, platinum and platinum iridium alloy, and most preferably is a platinum iridium alloy.

[25] The process according to any one of paragraphs [21] to [24], wherein the sacrificial outer element and/or the sacrificial core element comprise(s) a non-noble metal or non-noble metal alloy, preferably selected from the group of nickel, copper, steel, and alloys of each one of these metals.

[26] The process according to any one of paragraphs [21] to [25], wherein the sacrificial outer element and the sacrificial core element comprise a metal, and wherein the metal of the monolithic metal precursor has a higher standard electrode potential than the metal of the sacrificial outer element and the sacrificial core element.

[27] The process according to any one of paragraphs [21] to [26], wherein step 5) comprises a drawing process, which is preferably carried out with a deformation factor of between 5 and 40%, preferably between 15 and 30%, per individual drawing, and/or a die cast having a total included angle 2 α in the range of from 5 to 20°, preferably from 5 to 15°.

[28] The process according to any one of paragraphs [21] to [27], wherein an outer diameter of the sacrificial outer element provided in step 1) and the outer diameter of the formed composite obtained in step 5) have a ratio which is in the range of 60:1 to 2:1, preferably in the range of 30:1 to 5:1.

[29] A composite for preparing a ring electrode or a part thereof comprising
i) a sacrificial outer element comprising a cavity A', wherein the sacrificial outer element, as seen in a radial cross section, has a circular outer shape,
ii) a monolithic metal element comprising a tube comprising a cavity B', wherein the monolithic metal element is located in cavity A' of the sacrificial outer element,
iii) a sacrificial core element, wherein the sacrificial core element is located in cavity B' of the monolithic metal element.

[30] A ring electrode or a part thereof for a medical device,
wherein the ring electrode or the part thereof comprises a tube comprising a cavity, and
wherein the ring electrode or the part thereof is a monolithic metal, and
wherein the ring electrode or the part thereof, as seen in a radial cross section, has a non-circular outer shape.

[31] The ring electrode or the part thereof according to paragraph [30], wherein the ring electrode or the part thereof, as seen in a radial cross section, has an oval, polygonal, cubic or rectangular outer shape, and/or
wherein the cavity, as seen in a radial cross section, has a shape which is different to the outer shape of the ring electrode or the part thereof, and preferably has a circular shape.

[32] The ring electrode or the part thereof according to paragraph [30] or [31], wherein the tube has a wall, which at least in one section has a thickness of below 150 µm, and preferably in the range of 10 to 100 µm.

[33] The ring electrode or the part thereof according to any one of paragraphs [30] to [32], wherein the tube has at least one outer diameter in the range of 0.1 to 4 mm, and preferably of 0.2 to 2 mm, and/or
wherein the cavity has an inner diameter in the range of 0.01 to 3.8 mm, and preferably 0.05 to 1.8 mm

[34] A medical device comprising the ring electrode or the part thereof according to any one of paragraphs [30] to [33].

The features disclosed in the claims, the specification, and the drawings maybe essential for different embodiments of the claimed invention, both separately and in any combination with each other.

Example

Figure 1:
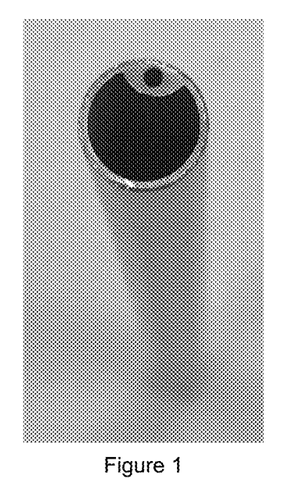
FIG. 1 illustrates an image of a monolithic metal precursor in a top view/cross section view.

A monolithic metal precursor consisting of platinum/iridium alloy (Pt/Ir10) was prepared by electrical discharging machining (EDM). The outer diameter of the precursor is 8 mm, and the length was 150 mm FIG. 1 illustrates an image of the precursor. The monolithic precursor was an outer tube having a first cavity and a wall, which had in one section an inner tube forming a second cavity. The monolithic metal precursor had the dimensions as illustrated in Table 1 below.

A first sacrificial core element consisting of nickel was provided. The nickel core element, as seen in a radial cross section, had essentially the profile of the first cavity formed by the outer tube of the Pt/Ir precursor.

A second sacrificial core element consisting of stainless steel (wire) was provided. The stainless steel wire, as seen in a radial cross section, had essentially the shape of the second cavity of the precursor.

A drawing process according to the present embodiments was carried out. A ring electrode was obtained with the dimensions as illustrated in Table 1. The dimensions of the ring electrode are also indicated in FIG. 2 which illustrates an image of the cross section of the ring electrode.

TABLE 1

| Dimension | Abbreviation | Precursor [mm] | Ring electrode [mm] | Factor |
|---|---|---|---|---|
| Outer diameter of outer tube | OD | 8.00 | 1.016 | 0.127 |
| Inner diameter of outer tube | ID | | 0.667 | |
| Wall thickness outer tube | WT1 | 0.598 | 0.075 | 0.125 |
| | WT2 | | 0.079 | |
| | WT3 | | 0.077 | |
| | WT4 | | 0.077 | |
| | WT5 | | 0.070 | |
| Diameter of inner tube | D | 2.165 | 0.278 | 0.128 |
| Inner diameter of inner tube | ID2 | 1.150 | 0.144 | 0.125 |
| | ID3 | 1.150 | 0.140 | 0.122 |

Figure 2:
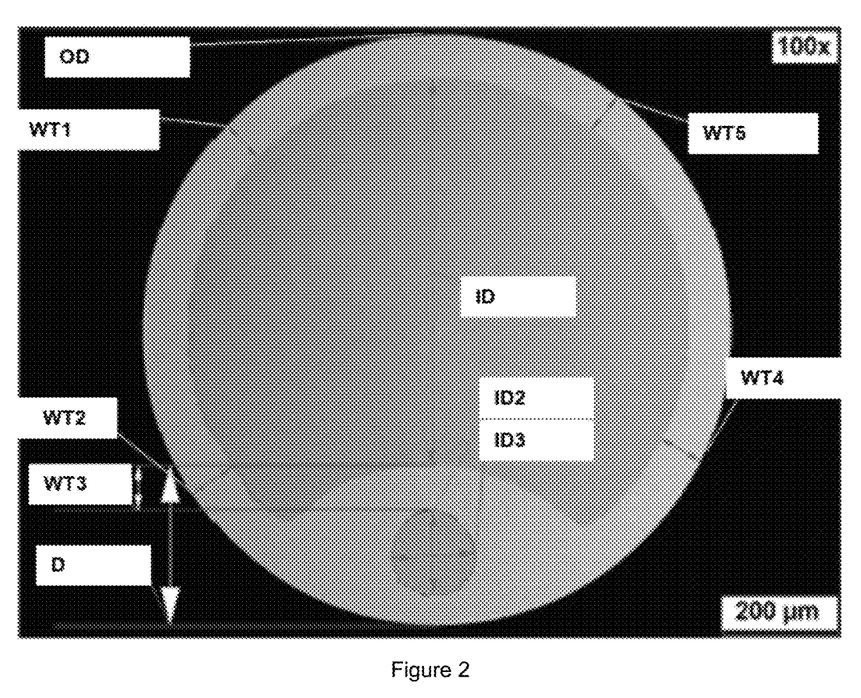
FIG. 2 illustrates an image of a radial cross section of a ring electrode prepared by the inventive process. The dimensions indicated in FIG. 2 are provided in Table 1.

As can be gathered from the results in Table 1 and FIG. 2, by the inventive process a ring electrode can be prepared, which has small dimensions and small wall thicknesses, and in which the geometry and shape of the precursor is essentially conserved, i.e. the dimensions vary in only very narrow tolerances. Thus, the precursor was uniformly drawn into the longitudinal direction.

Figure 3A:
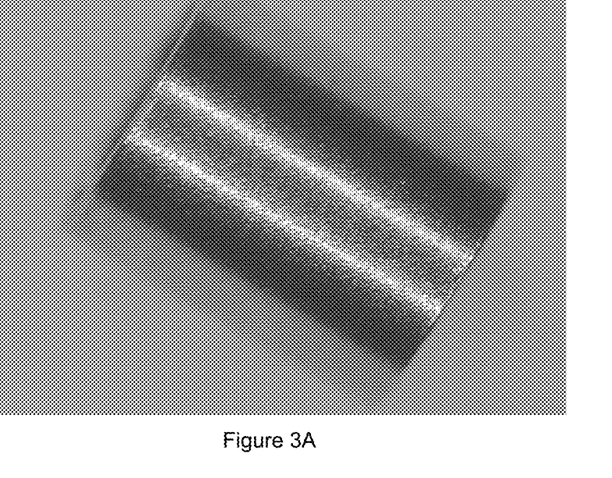
FIG. 3A illustrates an image of a ring electrode prepared by the inventive process in a side view.
Figure 3B:
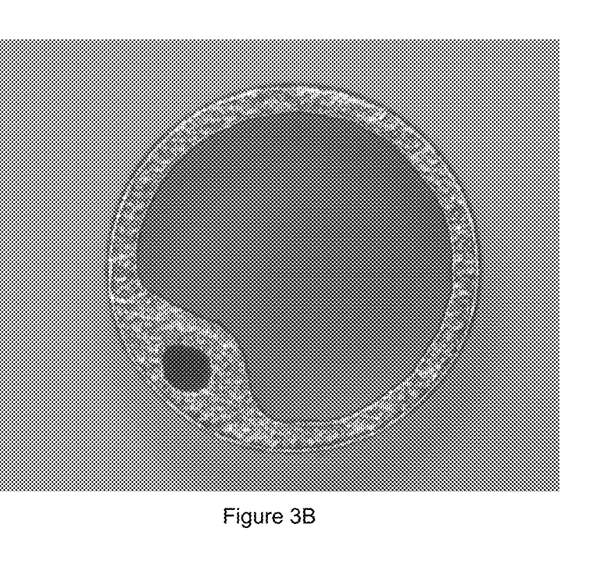
FIG. 3B illustrates an image of a ring electrode prepared by the inventive process in a radial cross section view.

A ring electrode according to one embodiment is also illustrated in FIG. 3A (side view) and FIG. 3B (cross section).

Although specific embodiments have been illustrated and described herein, it will be appreciated by those of ordinary skill in the art that a variety of alternate and/or equivalent implementations may be substituted for the specific embodiments illustrated and described without departing from the scope of the present embodiment. This application is intended to cover any adaptations or variations of the specific embodiments discussed herein. Therefore, it is intended that this embodiment be limited only by the claims and the equivalents thereof.

The invention claimed is:

1. A process for preparing a ring electrode comprising:
    a) providing a monolithic metal precursor,
        wherein the monolithic metal precursor comprises an outer tube forming a first cavity of the precursor, and wherein the outer tube has a wall comprising in one section an inner tube forming a second cavity of the precursor;

b) preparing a composite precursor by inserting a first sacrificial core element into the first cavity of the precursor provided in a) and a second sacrificial core element into the second cavity of the precursor provided in a);

c) forming the composite precursor obtained in b) to obtain a formed composite having a smaller outer diameter than the composite precursor obtained in b);

d) separating a composite disk from the formed composite obtained in c);

e) removing the first and the second sacrificial core element from the composite disk obtained in d).

2. The process according to claim 1, wherein the monolithic metal precursor is prepared by at least one process selected from the group of electrical discharging machining, additive manufacturing, deep-hole drilling, and milling.

3. The process according to claim 1, wherein the monolithic metal precursor comprises a metal selected from the group consisting of platinum, gold, iridium, steel, titanium, hafnium, niobium, tantalum, cobalt, nickel, chromium, zirconium, rhenium, tungsten, molybdenum, and alloys of each one of these metals, and selected from the group consisting of nickel cobalt alloy, steel, platinum and platinum iridium alloy, and wherein the first sacrificial core element or the second sacrificial core element comprise(s) a non-noble metal or non-noble metal alloy, selected from the group of nickel, copper, steel, and alloys of each one of these metals.

4. The process according to claim 1, wherein the inner tube is arranged on the inner side of the outer tube of the monolithic metal precursor provided in a), or wherein the outer tube of the monolithic metal precursor provided in a), as seen in a radial cross section, has a circular outer shape, and the section of the wall of the outer tube which comprises the inner tube protrudes into the first cavity of the outer tube.

5. The process according to claim 1, wherein the first and second sacrificial core elements inserted in b) comprise a metal, and wherein the metal of the monolithic metal precursor has a higher standard electrode potential than the metal of the first and the second sacrificial core elements.

6. The process according to claim 1, wherein c) comprises a drawing process, which is preferably carried out with a deformation factor of between 5 and 40%, per individual drawing, and a die cast having a total included angle 2 α in the range of from 5 to 20°.

7. The process according to claim 1, wherein c) comprises a drawing process, which is preferably carried out with a deformation factor of between 15 and 30%, per individual drawing, and a die cast having a total included angle 2 α in the range of from 5 to 15°.

8. The process according to claim 1, wherein the outer tube of the monolithic metal precursor provided in a) comprises at least one further inner tube forming at least one further cavity of the monolithic metal precursor in at least one further section of the wall, wherein b) further comprises inserting at least one further sacrificial core element in the at last one further cavity of the precursor, and wherein c) further comprises removing the at least one further sacrificial core element from the composite disk obtained in d).

9. The process according to claim 1, wherein the outer diameter of the outer tube of the monolithic metal precursor provided in a) and the outer diameter of the formed composite obtained in c) have a ratio which is in the range of 60:1 to 2:1.

10. The process according to claim 1, wherein the outer diameter of the outer tube of the monolithic metal precursor provided in a) and the outer diameter of the formed composite obtained in c) have a ratio which is in the range of 30:1 to 5:1.

11. A composite for preparing a ring electrode comprising i) a monolithic metal element comprising an outer tube forming a first cavity,
wherein the outer tube has a wall comprising in one section an inner tube forming a second cavity, ii) a first sacrificial core element, wherein the first sacrificial core element is located in the first cavity of the monolithic metal element, and iii) a second sacrificial core element, wherein the second sacrificial core element is located in the second cavity of the monolithic metal element.

12. A ring electrode for a medical device, wherein the ring electrode is a monolithic metal, wherein the ring electrode comprises an outer tube forming a first cavity of the electrode, wherein the outer tube has a wall comprising in one section an inner tube forming a second cavity of the electrode, and wherein the wall of the outer tube has at least one section having a thickness of below 150 μm.

13. The ring electrode according to claim 12, wherein the outer tube of the ring electrode has an outer diameter in the range of 0.2 to 5 mm, and wherein the first cavity formed by the outer tube has an inner diameter in the range of 0.05 to 4.8 mm, and wherein the second cavity formed by the inner tube has an inner diameter in the range of 0.01 to 1.0 mm.

14. The ring electrode according to claim 12, wherein the outer tube of the ring electrode has an outer diameter in the range of 0.5 to 2 mm, and wherein the first cavity formed by the outer tube has an inner diameter in the range of 0.1 to 1.8 mm, and wherein the second cavity formed by the inner tube has an inner diameter in the range of 0.05 to 0.3 mm.

15. A process for preparing a ring electrode or a part thereof, wherein the process comprises:

1) Providing a sacrificial outer element comprising a cavity A, wherein the sacrificial outer element, as seen in a radial cross section, has a circular outer shape;

2) Providing a monolithic metal precursor comprising a tube comprising a cavity B;

3) Providing a sacrificial core element;

4) Preparing a composite precursor by inserting the monolithic metal precursor into cavity A of the sacrificial outer element, and by inserting the sacrificial core element into cavity B of the monolithic metal precursor;

5) Forming the composite precursor obtained in 4) to obtain a formed composite having a smaller outer diameter than the composite precursor obtained in 4);

6) Separating a composite disk from the formed precursor obtained in 5);

7) Removing the sacrificial outer element and the sacrificial core element from the composite disk obtained in 6).

16. The process according to claim 15, wherein the outer shape of the monolithic metal precursor, as seen in a radial cross section, has a non-circular outer shape of, an oval, polygonal, cubic or rectangular outer shape, or wherein the cavity B of the monolithic metal precursor, as seen in a radial cross section, has a different shape than the outer shape of the monolithic metal precursor, or a circular shape.

17. A composite for preparing a ring electrode or a part thereof comprising:
  i) a sacrificial outer element comprising a cavity A', wherein the sacrificial outer element, as seen in a radial cross section, has a circular outer shape,
  ii) a monolithic metal element comprising a tube comprising a cavity B', wherein the monolithic metal element is located in cavity A' of the sacrificial outer element,
  iii) a sacrificial core element, wherein the sacrificial core element is located in cavity B' of the monolithic metal element.

18. A ring electrode or a part thereof for a medical device:
wherein the ring electrode or the part thereof comprises a tube comprising a cavity, and
wherein the ring electrode or the part thereof is a monolithic metal, and
wherein the ring electrode or the part thereof, as seen in a radial cross section, has a non-circular outer shape.

* * * * *